ABSTRACT

United States Patent [19]
Koda et al.

[11] Patent Number: 4,929,618
[45] Date of Patent: May 29, 1990

[54] PIPERDINE AND PIPERAZINE DERIVATIVES, AND ANTIHISTAMINIC PHARMACEUTICAL COMPOSITIONS CONTAINING THE SAME

[75] Inventors: Akihide Koda, Gifu; Jun'ichiro Kita, Ube; Yoshiaki Kuroki, Ube; Hiroshi Fujiwara, Ube; Shinji Takamura, Ube; Kayoko Yamano, Ube, all of Japan

[73] Assignee: Ube Industries, Ltd., Ube, Japan

[21] Appl. No.: 325,306

[22] Filed: Mar. 16, 1989

[30] Foreign Application Priority Data

Mar. 25, 1988 [JP] Japan .................................. 63-69711
Jul. 15, 1988 [JP] Japan ................................. 63-175142

[51] Int. Cl.$^5$ ................. A61K 31/495; A61K 31/445; C07D 417/14; C07D 401/14
[52] U.S. Cl. ..................................... 514/253; 514/318; 514/321; 514/322; 514/327; 544/360; 544/364; 544/369; 544/370; 546/193; 546/194; 546/198; 546/199; 546/221
[58] Field of Search ............... 544/360, 364, 369, 370; 546/193, 194, 198, 199, 222; 514/253, 318, 321, 322, 327

[56] References Cited

U.S. PATENT DOCUMENTS 4,250,176  2/1981  Vandenberk et al. ............. 544/360

Primary Examiner—Richard A. Schwartz
Assistant Examiner—Richard Sharpe
Attorney, Agent, or Firm—Frishauf, Holtz, Goodman & Woodward

[57] ABSTRACT

Disclosed is a compound represented by Formula (I):

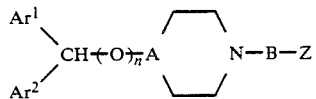

wherein $Ar^1$, $Ar^2$, n, A, B and Z are as defined in claims. Disclosed are also a process for preparing the compound and pharmaceutical compositions containing the compound.

The compound has an antihistamic and antiallergic effect.

49 Claims, No Drawings

PIPERDINE AND PIPERAZINE DERIVATIVES, AND ANTIHISTAMINIC PHARMACEUTICAL COMPOSITIONS CONTAINING THE SAME

BACKGROUND OF THE INVENTION

This invention relates to a novel piperidine derivative and a piperazine derivative, a process for preparing the same and an antihistaminic and antiallergic pharmaceutical composition containing the same.

Up to date, a large number of useful piperidine and piperazine derivatives have been found to be pharmacologically active components. Among these compounds, those with similar pharmacological activities and partially similar skeleton to the compounds of the present invention may include the compounds disclosed in Japanese Patent Publications Nos. 30990/1987 and 31707/1987, but in the said publications, there is no description at all about the group represented by the following Formula (II) possessed by the compounds of the present invention:

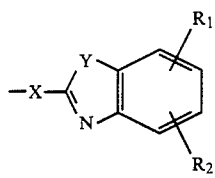

(wherein X and Y each independently are selected from the group consisting of >NH, —O— and —S—; $R_1$ and $R_2$ each independently represent a group selected from the group consisting of a hydrogen atom, a halogen atom, a lower alkyl group and a lower alkoxy group).

Also, Japanese Unexamined Patent Publication No. 129282/1987 discloses bicyclic condensed oxazoles and thiazoleamines which are partially similar in structure to the compounds of the present invention, but they are different in the piperidine site and their pharmacological activity is characterized by anti-Parkinson's disease, which is entirely different from the pharmacological activity of the compounds of the present invention.

Further, there are also similar compounds disclosed in Japanese Unexamined Patent Publication No. 94962/1985, but in the said publication, there is no description at all about a pyridyl group at the aryl moiety in the present invention.

Also, Japanese Unexamined Patent Publication No. 194068/1986 discloses vinyl derivatives and 5-lipoxygenase inhibitors containing the same, in which the structure partially similar to that of the compounds of the present invention are described, but they are different from the compounds of the present invention in structure at the moiety adjacent to carbonyl group and also have different pharmacological activity.

SUMMARY OF THE INVENTION

Most of the prior antihistaminic agents act on the central nervous system to induce sedative effect (sleepiness). The present inventors have studied intensively in order to synthesize novel piperidine and piperazine derivatives having effective pharmacological activity, and found that the novel piperidine and piperazine derivatives of the present invention and their pharmaceutically acceptable acid adducts have useful pharmacological properties, particularly strong antihistaminic and antiallergic activities, and yet have little potentiating effect of sleepiness induced by thiopental which is the central system inhibitor, and consequently accomplished the present invention.

The novel piperidine and piperazine derivatives of the present invention are compounds represented by Formula (I):

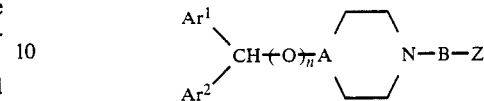

wherein $Ar^1$ and $Ar^2$ each independently represent a group selected from the group consisting of a phenyl group; phenyl groups having a halogen atom, a nitro group, a lower alkoxy group, a lower alkyl group or a lower alkyl group substituted with halogen atoms; and a pyridyl group; n is an integer of 0 or 1; A is a group selected from the group consisting of >N— and >CH—, with the proviso that when A is >N—, n is 0, and when A is >CH—, n is 1; B represents an alkylene group or an alkenylene which may be a straight chain having 2 to 6 carbon atoms or a branched chain having at least 2 carbon atoms in the main chain; Z is represented by Formula (II):

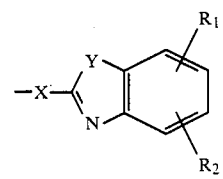

(wherein X and Y each independently represent a group selected from the group consisting of >NH, —O— and —S—, $R_1$ and $R_2$ each independently represent a group selected from the group consisting of a hydrogen atom, a halogen atom, a lower alkyl group and a lower alkoxy group) or by Formula (II'):

(wherein Z' represents a group selected from the group consisting of a lower alkyl group, a hydroxyl group, a lower alkoxy group, a phenoxy group, an amino group, a lower alkylamino group, an anilino group, a phenyl group and a phenyl group substituted with a lower alkyl group, with the proviso that when Z' is a phenyl group or a phenyl group substituted with a lower alkyl group, at least either one of the said $Ar^1$ and $Ar^2$ is a pyridyl group, and when Z is represented by Formula (II'), A is >CH and n is 1), and their pharmaceutically acceptable acid adducts.

DESCRIPTION OF THE PREFERRED EMBODIMENTS

In the present specification, the "lower" means to have 1 to 4 carbon atoms unless otherwise specifically noted.

In the above Formula (I), examples of the group represented by $Ar^1$ or $Ar^2$ may include phenyl group; a phenyl group substituted with a halogen atom such as 4-fluorophenyl, 2-chlorophenyl, 3-chlorophenyl, 4-chlorophenyl, 2-bromophenyl, 4-bromophenyl, 2- iodophenyl, 4-iodophenyl, etc.; a phenyl group substituted with alkyl groups such as 2-methyl, 3-methyl, 4-methyl, 2,4-dimethyl, 3,4-dimethyl, 4-ethyl, 4-isopropyl, 4-n-propyl, 4-n-butyl, etc.; a phenyl group substituted with a trifluoromethyl group; a phenyl group substituted with alkoxy groups such as 4-methoxy, 2,4-dimethoxy, 3,4-dimethoxy, 4-ethoxy, etc.; a phenyl groups substituted with a nitro group such as 2-nitro, 3-nitro, 4-nitro, etc.; or a pyridyl group such as 2-pyridyl, 3-pyridyl, 4-pyridyl, etc.; and at least one of $Ar^1$ and $Ar^2$ should be preferably a pyridyl group.

n is an integer of 0 or 1, A represents a member selected from the group consisting of >N— and >CH—, and when A is >N—, n is 0, and when A is >CH—, n is 1; B represents an alkylene or alkenylene group which may be straight chain or a branched chain having at least 2 carbon atoms in the main chain, and the said alkylene group is exemplified by an ethylene group, a propylene group, a trimethylene group, a tetramethylene group, a pentamethylene group, a hexamethylene group, etc., and the said alkenylene group is exemplified by a vinylene group, a propenylene group, a 2-butenylene group, a 2-pentenylene group, a 3-pentenylene group, etc., and a straight alkylene group or an alkenylene group having 2 to 5 carbon atoms are preferred.

Z is represented by Formula (II):

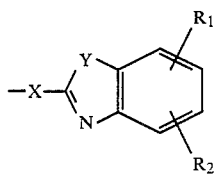

(wherein X and Y each independently represent a group selected from the group consisting of >NH—, —O—, and —S—; $R_1$ and $R_2$ each independently represent a group selected from the group consisting of a hydrogen atom; a halogen atom such as fluorine, chlorine, bromine, etc.; a lower alkyl group such as methyl, ethyl, propyl, etc.; a lower alkoxy group such as methoxy, ethoxy, propoxy, etc.) or by Formula (II'):

In the formula, Z' represents a lower alkyl group such as methyl, ethyl, propyl, isopropyl, cyclopropyl, butyl, isobutyl, t-butyl, cyclobutyl and the like; hydroxyl group; a lower alkoxy group such as methoxy, ethoxy, propoxy, isopropoxy, butoxy, isobutoxy, t-butoxy and the like; an amino group; a lower alkylamino group such as methylamino, dimethylamino, ethylamino, diethylamino, propylamino, isopropylamino, butylamino, isobutylamino, t-butylamino and the like; an anilino group; a phenyl group; a phenyl group substituted with a lower alkyl group such as methylphenyl, ethylphenyl, propylphenyl, isopropylphenyl, butylphenyl, isobutylphenyl, t-butylphenyl and the like, preferably hydroxyl group, its ester, its amide or the like.

However, when Z' is a phenyl group or a phenyl group substituted with a lower alkyl group, at least one of the above $Ar^1$ or $Ar^2$ is a pyridyl group, and when Z is represented by Formula (II'), A is >CH— and n is 1.

In the following, examples of representative compounds of the present invention are enumerated, but the compounds of the present invention are not limited to these compounds as a matter of course.

2-[2-[4-[(4-Chlorophenyl)-2-pyridylmethoxy]-1-piperidyl]-ethylthio]benzoxazole;

5-Chloro-2-[2-[4-[(4-chlorophenyl)-2-pyridylmethoxy]-1-piperidyl]ethylthio]benzoxazole;

5-Chloro-2-[2-[4-(diphenylmethoxy)-1-piperidyl]ethylthio]benzoxazole;

2-[2-[4-[(4-Chlorophenyl)-2-pyridylmethoxy]-1-piperidyl]-ethylthiobenzoxazole fumarate;

2-[3-[4-[(4-Chlorophenyl)-2-pyridylmethoxy]-1-piperidyl]-propylthio]benzoxazole;

2-[2-[4-[(4-Chlorophenyl)-2-pyridylmethoxy]-1-piperidyl]-ethylthio]-6-methylbenzoxazole;

2-[2-[4-[(4-Chlorophenyl)-2-pyridylmethoxy]-1-piperidyl]-ethyloxy]benzoxazole;

2-[2-[4-[(4-Chlorophenyl)-2-pyridylmethoxy]-1-piperidyl]-ethylamino]benzoxazole;

2-[2-[4-[(4-Chlorophenyl)-2-pyridylmethoxy]-1-piperidyl]-ethylamino]benzoxazole fumarate;

2-[2-[4-[(4-Chlorophenyl)-2-pyridylmethoxy]-1-piperidyl]-ethylthio]benzothiazole;

2-[3-[4-[(4-Chlorophenyl)-2-pyridylmethoxy]-1-piperidyl]-propylthio]benzothiazole;

2-[3-[4-[(4-Chlorophenyl)-2-pyridylmethoxy]-1-piperidyl]-propylthio]-6-ethoxybenzothiazole;

2-[2-[4-[(4-Chlorophenyl)-2-pyridylmethoxy]-1-piperidyl]-ethylamino]benzothiazole;

2-[2-[4-(Diphenylmethyl)-1-piperadinyl]ethylthio]benzothiazole;

2-[3-[4-(Diphenylmethyl)-1-piperadinyl]propylthio]-benzothiazole;

2-[3-[4-(Diphenylmethyl)-1-piperadinyl]propylthio]-benzothiazole dimaleate;

2-[3-[4-(Diphenylmethyl)-1-piperadinyl]propylthio]-benzimidazole;

3-[4-[(4-Chlorophenyl)-2-pyridylmethoxy]-1-piperidyl]-propionic acid;

Ethyl 3-[4-[(4-chlorophenyl)-2-pyridylmethoxy]-1-piperidyl]propionate;

4-[4-[(4-Chlorophenyl)-2-pyridylmethoxy]-1-piperidyl]-butanoic acid;

Ethyl 4-[4-[(4-chlorophenyl)-2-pyridylmethoxy]-1-piperidyl]butanoate and its p-toluenesulfonic acid adduct;

4-[4-[(4-Chlorophenyl)-2-pyridylmethoxy]-1-piperidyl]-butaneamide and its maleic acid adduct Ethyl 4-(4-diphenylmethoxy-1-piperidyl)butanoate and its fumaric acid adduct;

Ethyl 4-[4-(phenyl-2-pyridylmethoxy)-1-piperidyl]-butanoate and its p-toluenesulfonate;

Ethyl 4-[4-(phenyl-3-pyridylmethoxy)-1-piperidyl]-butanoate and its p-toluenesulfonate;

Ethyl 4-[4-[(4-chlorophenyl)-phenylmethoxy]-1-piperidyl]butanoate and its p-toluenesulfonate;

Ethyl 4-[4-(4,4'-dimethoxyphenylmethoxy)-1-piperidyl]-butanoate and its p-toluenesulfonate;

Ethyl 4-[4-(4,4'-difluorophenylmethoxy)-1-piperidyl]-butanoate and its p-toluenesulfonate;

Ethyl 4-[4-[(4-methylphenyl)-phenylmethoxy]-1-piperidyl]-butanoate;

Propyl 4-[4-[(4-chlorophenyl)-2-pyridylmethoxy]-1-piperidyl]butanoate and its p-toluenesulfonate;

Ethyl 4-[4-[(4-chlorophenyl)-2-pyridylmethoxy]-1-piperidyl]-2-butenoate;

5-[4-[(4-Chlorophenyl)-2-pyridylmethoxy]-1-piperidyl]-2-pentanone and its fumarate;

4-[(4-Chlorophenyl)-2-pyridylmethoxy]-1-(3-benzoyl-propyl)piperidine;

4-[(4-Chlorophenyl)-2-pyridylmethoxy]-1-[3-(4-tert-butylbenzoyl)propyl]piperidine.

According to the present invention, the compound represented by the above Formula (I) can be prepared by Processes 1 to 5 shown by the following Reaction Schemes 1 to 5.

Process 1

Reaction Scheme 1:

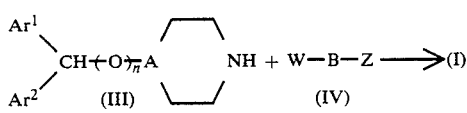

(wherein W is a leaving group, for example, a halogen atom such as chlorine, bromine, iodine, etc., or a reactive ester group such as a methanesulfonyloxy group, a p-toluenesulfonyloxy group, etc., $Ar^1$, $Ar^2$, n, A, B and Z are the same as defined above).

Compound (I) can be prepared easily by reacting Compound (III) with Compound Formula (IV) as shown in Reaction Scheme (1).

Compound (IV) is added in an amount of 1 to 3 mols to 1 mol of Compound (III).

The above reaction is carried out in an appropriate organic solvent inert to the said reaction. Examples of appropriate organic solvents may include lower alcohols such as methanol, ethanol, propanol, butanol, etc.; aromatic hydrocarbons such as benzene, toluene, xylene, etc.; ethers such as 1,4-dioxane, THF, etc.; ketones such as acetone, ethyl methyl ketone, methyl isobutyl ketone, etc.; amides such as N,N-dimethylformamide, etc.; or solvent mixtures of two or more of these solvents. Also, the reaction may be preferably carried out in the presence of a base. Examples of such base may include alkali metal hydroxides such as sodium hydroxide, etc.; alkaline earth metal hydroxides such as calcium hydroxide, etc.; alkali metal carbonates such as potassium carbonate, etc.; alkaline earth metal carbonates such as calcium carbonate, etc.; alkali metal hydrogen carbonates such as sodium hydrogen carbonate, etc.; alkali metal hydrides such as sodium hydride, etc.; alkaline earth metal hydrides such as calcium hydride, etc.; alkoxides of alkali metal such as sodium methoxide, etc.; trialkylamines such as triethylamine, etc.; and pyridine and so on. These bases are added in an amount of 1 to 3 mols to 1 mol of Compound (III).

Also, as the reaction accelerator, a small amount of an appropriate metal iodide such as sodium or potassium iodide may be added. For enhancing the reaction rate, it is preferable to carry out the reaction at a slightly elevated temperature, and it is also possible in some cases to carry out the reaction at a reflux temperature of the reaction mixture. The reaction time may be 2 to 24 hours.

The reaction product is separated from the reaction mixture, and may be further purified according to a method generally known in the art, if necessary.

Process 2

Reaction Scheme (2):

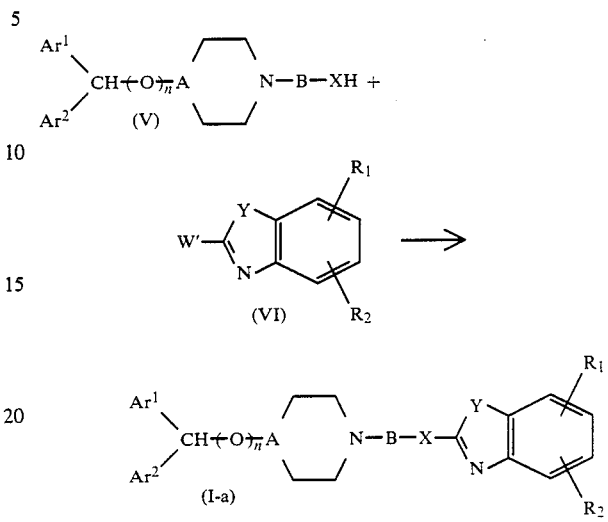

(wherein W' is a leaving group, for example, a halogen atom such as chlorine, bromine, iodine, etc., and $Ar^1$, $Ar^2$, n, A, B, X, Y, $R_1$ and $R_2$ are the same as defined above).

Compound (I-a) can be easily prepared by reacting Compound (V) with Compound (VI) as shown in Reaction Scheme (2).

This reaction can be carried out substantially in the same manner as in Process 1.

Process 3

Reaction Scheme 3:

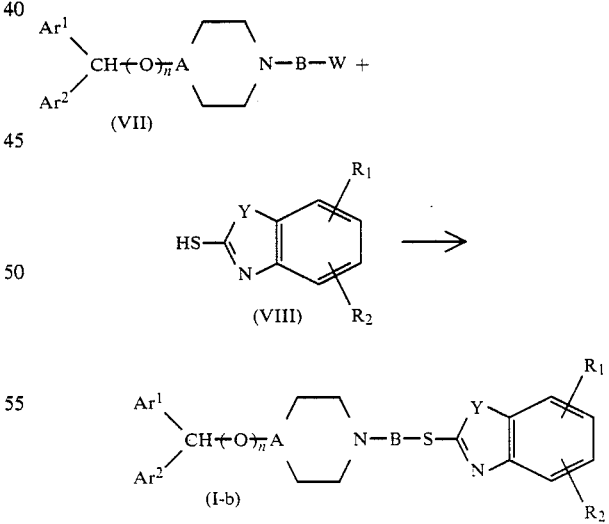

(wherein $Ar^1$, $Ar^2$, n, A, B, W, Y, $R_1$ and $R_2$ are the same as defined above).

Compound (I-b) can be easily prepared by reacting Compound (VII) with Compound Formula (VIII) as shown in Reaction Scheme (3).

This reaction can be carried out substantially in the same manner as in Process 1.

Process 4

In the above Formula (I) and (II'), when Z' represents a lower alkoxy group, a phenoxy group, an amino group, a lower alkylamino group or a anilino group, the compound of the present invention can be prepared in the following process.

Reaction Scheme 4:

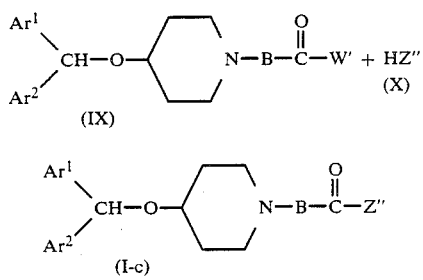

(wherein W' is a leaving group, for example, a halogen atom such as chlorine, bromine, iodine, etc. or a hydroxyl group, Z" is a group selected from the group consisting of a lower alkoxy group, a phenoxy group, an amino group, a lower alkylamino group and an anilino group; and Ar¹, Ar² and B are the same as defined above).

Compound (I-C) can be prepared easily by reacting Compound (IX) with Compound Formula (X) as shown in Reaction Scheme (4). Compound (X) is added in an amount of 1 to 3 mols to 1 mol of Compound (IX).

When W' represents a halogen atom, Compound (IX) can be obtained by converting the corresponding carboxylic acid to the said halide according to the known method. In this case, the reaction shown in Reaction Scheme (4) is carried out in an inert solvent at −5° to 30° C., and the reaction time may be 1 to 10 hours.

When W' is hydroxyl group, the reaction shown in Reaction Scheme (4) is carried out in an inert solvent in the presence of a dehydrating agent such as dicyclohexylcarbodiimide, anhydrous trifluoroacetic acid, N-acylimidazole, etc. The dehydrating agent is used in an amount of 1 to 2 mols to 1 mol of Compound (IX), and the reaction temperature is −5° to 30° C. and the reaction time is 1 to 24 hours.

Process 5

When Z' in the above Formula (I) and (II') represents hydroxy group, the compound of the present invention can be prepared in the following process.

Reaction Scheme 5:

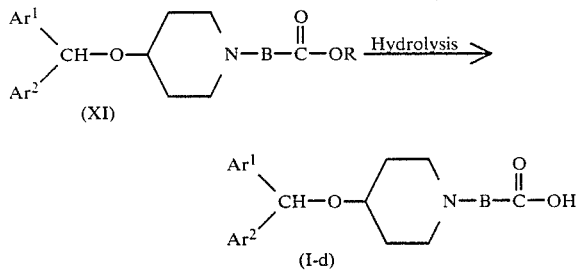

(wherein R is a lower alkyl group such as methyl, ethyl, etc., and Ar¹, Ar² and B are the same as defined above).

Compound (I-d) can be easily prepared by hydrolyzing Compound (XI) under basic conditions as shown in Reaction Scheme (5). This hydrolysis should be preferably carried out in aqueous alcohols such as aqueous methanol, ethanol, etc. by using an inorganic base such as sodium hydroxide, potassium hydroxide, etc. in an amount of 1 to 5 mol to 1 mol of Compound (XI) at room temperature or at a slightly elevated temperature for increasing the reaction rate, and in some cases, the reaction can be also carried out at a reflux temperature of the reaction mixture. The reaction time may be 1 to 10 hours.

Concerning piperidine derivatives and piperazine derivatives used as the starting material, the intermediate product (III-a), wherein A is >N— and n is 0 is generally known (C.A. 44: 7327d (1950), C.A. 64: 3499e (1966), etc.), and all of them can be prepared by application of the processes known in this field of the art. Such intermediate products can be prepared by, for example, subjecting an appropriate aroyl halide to Friedel-Crafts reaction by using an appropriate areve to obtain Ar¹, Ar²-methanone, which is then reduced in a conventional manner to the corresponding methanol by use of, for example, sodium borohydride. Then, the alcohol obtained is converted according to the generally known procedure into a diarylhalogenomethane or a reactive ester (XII) (wherein W is a halogen atom such as chlorine, bromine, etc. or a reactive ester group such as p-toluenesulfonyloxy group, and Ar¹ and Ar² are the same as defined above), and then the desired intermediate product (III-a) is obtained from the reaction of Compound (XII) with piperazine (XIII).

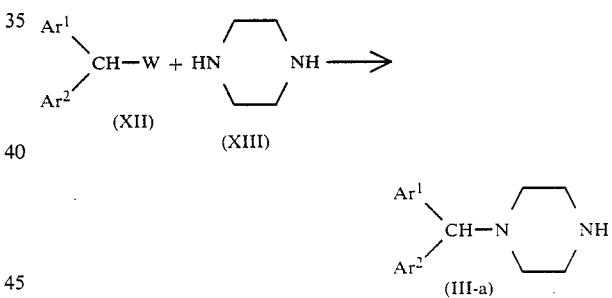

The intermediate product (III-b), wherein A is >CH— and n is 1, can be easily prepared by O-alkylation of Compound (XIV) (wherein Q represents a general protecting group used for amino group such as formyl group, an ethoxycarbonyl group, a tert-butoxycarbonyl group, represented by Compound (XII)) with a halide or a reactive ester, and then followed by elimination of the protecting group from Compound (XV) in a general method.

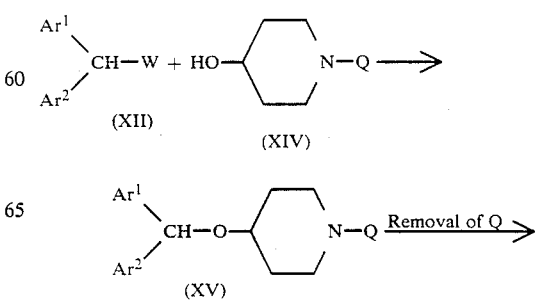

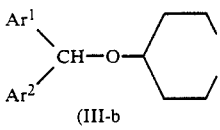

(III-b)

By reacting an appropriate acid with Compound (I) of the present invention, a non-toxic, pharmacologically effective acid adduct can be obtained. In this case, examples of appropriate acid may include hydro-halogenic acids such as hydrochloric acid, hydrobromic acid, etc.; inorganic acids such as sulfuric acid, nitric acid, phosphoric acid, etc.; and organic acids such as acetic acid, propionic acid, hydroxyacetic acid, 2-hydroxypropionic acid, pyruvic acid, malonic acid, succinic acid, maleic acid, fumaric acid, dihydroxyfumaric acid, oxalic acid, benzoic acid, cinnamic acid, salicylic acid, methanesulfonic acid, ethanesulfonic acid, benzenesulfonic acid, p-toluenesulfonic acid, cyclohexysulfaminic acid, 4-aminosalicylic acid, etc.

The compounds of the present invention represented by Formula (I) and their pharmaceutically acceptable acid adducts have useful pharmacological properties, particularly potent antihistaminic and antiallergic activities. Further, they have the specific feature that the secondary effect such as stimulation or inhibition on the central nervous system frequently observed in the prior antihistaminic agents can be reduced to a minimum, and they can be used themselves or in combination with appropriate carrier as effective drugs for therapy for human being and animals. Specifically, they can be applied for therapy or treatment of allergic skin diseases such as urticaria, eczema, dermatitis, etc., and sternutatio, pituita and cough, caused by upper respiratory track inflammation and bronchial asthma, etc.

When the compound of the present invention is used as the antihistaminic agent, it may be administered primarily orally or by many of external application. The dose may be appropriately increased or decreased depending on the difference in disease, the extent of symptom, age, etc., and may be generally about 2 to 50 mg, preferably 5 to 25 mg for an adult per day.

To form the compound of the present invention into a preparation, it can be formed into a dosage form such as tablet, capsule, powder, syrup, ointment, etc. according to conventional methods in the technical field of preparation.

In general, the compound of the present invention can relax smooth muscle of trachea and either in vitro or in vivo, and can significantly inhibit death induced by histamine hydrochloride in a guinea pig to which the compound is orally administered at a dose of 1 mg per 1 kg of the animal body weight. Also, when the influence of these components on the persisting time of the anesthetic action induced by thiopental as the central nerve inhibiting agent was examined, substantially no remarkable potentiating effect was recognized. The pharmacological test results for the following representative compounds from the present invention are shown below.

Compound A:
2-[2-[4-[(4-Chlorophenyl)-2-pyridylmethoxy]-1-piperidyl]-ethylthio]benzoxazole (prepared in Example 1)

Compound B:
2-[2-[4-[(4-Chlorophenyl)-2-pyridylmethoxy]-1-piperidyl]-ethylthio]benzoxazole fumarate (prepared in Example 2)

Compound C:
2-[2-[4-[(4-Chlorophenyl)-2-pyridylmethoxy]-1-piperidyl]-propylthio]benzoxazole (prepared in Example 9)

Compound D:
2-[2-[4-[(4-Chlorophenyl)-2-pyridylmethoxy]-1-piperidyl]-ethylamino]benzoxazole fumaric acid salt (prepared in Example 14)

Compound E:
2-[2-[4-[(4-Chlorophenyl)-2-pyridylmethoxy]-1-piperidyl]-ethylthio]benzothiazole (prepared in Example 15)

Compound F:
2-[3-[4-[(4-Chlorophenyl)-2-pyridylmethoxy]-1-piperidyl]-propylthio]benzothiazole (prepared in Example 16)

Compound G:
2-[3-[4-[(4-Chlorophenyl)-2-pyridylmethoxy]-1-piperidyl]-propylthio-6-ethoxybenzothiazole fumarate (prepared in Example 18)

Compound H:
2-[2-[4-[(4-Chlorophenyl)-2-pyridylmethoxy]-1-piperidyl]-ethylamino]benzothiazole (prepared in Example 19)

Compound I:
2-[3-[4-[(4-Diphenylmethyl)-1-piperadinyl]propylthio]-benzothiazole dimalate (prepared in Example 22)

Compound J:
Ethyl 4-[4-[(4-chlorophenyl)-2-pyridylmethoxy]-1-piperidyl]butanoate (prepared in Example 26)

Compound K:
Ethyl 4-[4-[(4-chlorophenyl)-2-pyridylmethoxy]-1-piperidyl]butanoate p-toluenesulfonate (prepared in Example 27)

Compound L:
4-[4-[(4-Chlorophenyl)-2-pyridylmethoxy]-1-piperidyl]-butanoic acid (prepared in Example 28)

Compound M:
4-[4-[(4-Chlorophenyl)-2-pyridylmethoxy]-1-piperidyl]-butanamide maleate (prepared in Example 30)

Compound N:
Ethyl 4-(4-diphenylmethoxy-1-piperidyl)butanoate fumaric acid salt (prepared in Example 35)

Compound O:
Ethyl 4-[4-[(4-chlorophenyl)-2-pyridylmethoxy]-1-piperidyl]-2-butenoate (prepared in Example 46)

Compound P:
5-[4-[(4-Chlorophenyl)-2-pyridylmethoxy]-1-piperidyl]-2-pentanone fumaric acid salt (prepared in Example 48)

Compound Q:
4-[(4-Chlorophenyl)-2-pyridylmethoxy]-1-(3-benzoylpropyl)piperidine (prepared in Example 49)

Pharmacological test

Protective effect on histamine-induced death

Hartley-strain male guinea pigs weighing 200 to 250 g were employed. After the test animals were starved for 5 hours, the test substance was orally administered at a dose of 1 mg/kg. 2 hours later after administration of the test substance, 1.25 mg/kg of histamine hydrochloride was intravenously administered to induce histamine shock. The potency of the test substance was judged by the percent inhibition of death induced by histamine. The test results are shown in Table 1.

Elongating effect on thiopental-induced anesthesia.

ddY-strain male mice of 5 weeks of age were employed. Thiopental sodium was dissolved in physiological saline, and the test substance was prepared with a suspending agent of 0.5% Tween 80 (trade name, produced by Atlas Powder Co.; polyoxyethylene (20) sorbitan mono-oleate) and 1% gum tragacanth in the ratio of 1:2.5. The test animals were starved for 4 hours, 60 mg/10 ml/kg of the test substance was intraperitoneally administered (or orally administered), and then 20 minutes later (1 hour later in the case of oral administration), 30 mg/10 mg/kg of thiopental sodium was intravenously administered. The time immediately from intravenous administration to the righting reflex was measured, and this was defined as the anesthetic time. The formula for determining the anesthesia elongation is shown below.

$$\text{Anesthesia elongation} = \frac{\text{Anesthetic time for the group administered with test substance}}{\text{Anesthetic time for control group}}$$

The test results are shown in Table 1.

TABLE 1

| Test compound | Percent inhibition of histamine-induced death at a dose of 1 mg/kg, P.D. (%) | The ratio of the elongation on the anesthetic time induced by thiopental |
| --- | --- | --- |
| Control | 0 | 1.00 (i.p., p.o.) |
| Chlorophenylamine maleate | 100 | 1.81 (i.p.) |
| Astemizole | 100 | 1.51 (i.p.) |
| Terfenadine | 50 | 1.11 (i.p.) |
| Meqiutazine | 80 | 7.72 (i.p.) |
| Azelastine hydrochloric acid | 100 | 7.69 (p.o.) |
| Oxatomide | 100 | 4.56 (p.o.) |
| A | 100 | 0.89 (i.p.) |
| B | 100 | 1.21 (p.o.) |
| C | 100 | 0.91 (i.p.) |
| D | 100 | 0.88 (p.o.) |
| E | 60 | 1.02 (i.p.) |
| F | 80 | 1.73 (i.p.) |
| G | 100 | 0.92 (p.o.) |
| H | 100 | 1.05 (i.p.) |
| I | 80 | 1.25 (i.p.) |
| J | 100 | 1.04 (i.p.) |
| K | 100 | 1.19 (p.o.) |
| L | 100 | 1.14 (i.p.) |
| M | 100 | 0.75 (p.o.) |
| N | 80 | 0.90 (p.o.) |
| O | 100 | 1.14 (p.o.) |
| P | 100 | 0.86 (p.o.) |
| Q | 100 | 1.25 (p.o.) |

Therapy for allergy relies primarily on inhibition of the release of chemical mediators, or inhibition of interaction between Chemical mediators and specific receptors of them, and antihistaminic agent known as an $H_1$ receptor antagonist plays an important role. However, an $H_1$ receptor exists not only in the peripheral system, but also in the central nervous system, and when the antihistamine agent blocks the central system receptors, undesirable side-effect of sedation (sleepiness) is brought about. Therefore, it is desirable to prevent the influx of the drug into the central system to minimize the side-effect. In other words, a drug which can hardly pass through the blood-cerebral barrier led to the central nervous system, and interacts only with the peripheral $H_1$ receptor is preferred. Terfanadine and Astemizole as control drugs are reported to have little sedative side-effect.

From the test results summarized in Table 1, of the above 6 compounds used as control drugs, other than Telfenadine, all the drugs were confirmed to increase significantly the sleeping time induced by thiopental.

The novel piperidine and piperazine derivatives which are the compounds of the present invention have generally little potentiating activity for thiopental, and therefore no remarkable elongation of sleeping time is recognized, and yet they have more potent antihistaminic activity than Terfenadine. Also, the compounds of the present invention are extremely safe, and can be used continuously for a long term as pharmaceuticals, and were confirmed to have good tolerability in the toxicity test in mice by oral administration. In the case of the compound B, the LD50 for male mouse was found to be 1,700 mg/kg, and in the case of the compound D, it was 740 mg/kg, and in the case of the compound K, it was found to be 2,200 mg/kg.

The present invention is described below in more detail by referring to the following Examples, but the compounds mentioned below are set forth for further detailed description of the present invention and will not limit the scope of the present invention at all.

EXAMPLE 1

After 1.21 g (4.00 mmol) of 4-[(4-chlorophenyl)-2-pyridylmethoxy]piperidine and 0.97 g (3.76 mmol) of 2-(2-bromoethylthio)benzoxazole were dissolved in 10 ml of dioxane, 0.55 g of potassium carbonate was added to the mixed solution, and the mixture was heated under stirring at an oil bath temperature of 60° to 65° C. for 5 hours. After the reaction, the insolubles were filtered off, and the filtrate was concentrated under reduced pressure. The residue was separated by silica gel column chromatography using chloroform as an eluent. The fractions of the desired compound isolated was concentrated under reduced pressure to give 1.51 g (84%) of 2-[2-[4-[(4-chlorophenyl)-2-pyridylmethoxy]-1-piperidyl]ethylthio]benzoxazole as an oil.

Mass analysis value: EI-MS m/e=479(M+), CI-MS m/e=480(M++1)

$^1$H-NMR(CDCl$_3$): δ(ppm)=1.75(2H, b), 1.85(2H, b), 2.25(2H, m), 2.77(2H, t), 2.80(2H, b), 3.45(2H, t), 3.49(1H, m), 5.60(1H, s), 7.10–7.72(11H, m), 8.51(1H, m)

EXAMPLE 2

0.48 g (1.00 mmol) of 2-[2-[4-[(4-chlorophenyl)-2-pyridylmethoxy]-1-piperidyl]ethylthio]benzoxazole obtained in Example 1 and 0.116 g (1.00 mmol) of fumaric acid were dissolved in 20 ml of ethanol, and the mixed clean solution was concentrated under reduced pressure. The residue was crystallized from isopropyl ether. The product was recrystallized from ethyl acetate to give 0.50 g (84%) of 2-[2-[4-[(4-chlorophenyl)-2-pyridylmethoxy]-1-piperidyl]ethylthio]benzoxazole fumarate.

mp 154° to 156° C.

Elemental analysis value: Calcd. (for C$_{30}$H$_{30}$ClN$_3$O$_6$S 1/4H$_2$O): C 59.99 H 5.12 N 7.00 Found: C 60.19 H 5.13 N 6.96.

EXAMPLE 3

From (+)-tartaric acid, 2-[2-[4-[(4-chlorophenyl)-2-pyridylmethoxy]-1-piperidye]-ethylthio]benzoxazole (+)-tartarate was obtained in the same method as described in Example 2.

mp 92° to 97° C.

Elemental analysis value: Calcd. (for $C_{30}H_{32}ClN_3O_8S\ H_2O$): C 55.60 H 5.28 N 6.48 Found: C 55.89 H 5.23 N 6.20.

EXAMPLE 4

From citric acid, 2-[2-[4-[(4-chlorophenyl)-2-pyridylmethoxy]-1-piperidyl]ethylthio]benzoxazole citrate was obtained in the same method as described in Example 2.

mp 88° to 92° C.

Elemental analysis value: Calcd. (for $C_{32}H_{34}ClN_3O_9S\ H_2O$): C 55.69 H 5.25 N 6.09 Found: C 55.99 H 5.28 N 5.79.

EXAMPLE 5

From oxalic acid, 2-[2-[4-[(4-chlorophenyl)-2-pyridylmethoxy]-1-piperidyl]ethylthio]benzoxazole oxalate was obtained in the same method as described in Example 2.

mp 166° to 169° C.

Elemental analysis value: Calcd. (for $C_{28}H_{28}ClN_3O_6S$): C 59.00 H 4.95 N 7.37 Found: C 58.85 H 5.16 N 7.14.

EXAMPLE 6

After 2.00 g (6.60 mmol) of 4-[(4-chlorophenyl)-2-pyridylmethoxy]piperidine and 2.39 g (8.17 mmol) of 2-(2-bromoethylthio)-5-chlorobenzoxazole were dissolved in 10 ml of dioxane, 1.10 g (7.96 mmol) of potassium carbonate was added to the mixed solution, and the mixture was stirred at an oil bath temperature of 75° to 80° C. for 6 hours. After the reaction, the insolubles were filtered off, and the filtrate was concentrated under reduced pressure. The residue was separated by silica gel column chromatography with a mixed solution of chloroform and methanol in the volume ratio 50:1 as an eluent. The desired fraction was concentrated to give 1.83 g (54%) of 5-chloro-2-[2-[4-[(4-chlorophenyl)-2-pyridylmethoxy]-1-piperidyl]ethylthio]benzoxazole as an oily product.

Mass analysis value: EI-MS m/e=513(M+), CI-MS m/e=514(M+ +1).

$^1$H-NMR(CDCl$_3$): δ(ppm)=1.74(2H, b), 1.87(2H, b), 2.26(2H, b), 2.77(2H, t), 2.80(2H, b), 3.44(2H, t), 3.49(1H, m), 5.60(1H, s), 7.12–7.72(10H, m), 8.51(1H, m).

EXAMPLE 7

Using 4-diphenylmethoxy-1-piperidine and 2-(2-bromoethylthio)-5-chlorobenzoxazole, the reaction was carried out as described in Example 6, and the colorless crystals obtained were recrystallized from isopropyl ether to give 5-chloro-2-[2-[4-(diphenylmethoxy)-1-piperidyl]ethylthio]benzoxazole.

mp 98°–101° C.

$^1$H-NMR(CDCl$_3$): δ(ppm)=1.72(2H, b), 1.85(2H, b), 2.27(2H, b), 2.77(2H, t), 2.81(2H, b), 3.44(2H, t+m), 5.51(1H, s), 7.17–7.41(12H, m), 7.55(1H, d).

EXAMPLE 8

After 1.00 g (3.30 mmol) of 4-[(4-chlorophenyl)-2-pyridylmethoxy]piperidine and 1.08 g (3.97 mmol) of 2-(2-bromoethylthio)-6-methylbenzoxazole were dissolved in 12 ml of acetone, and 0.47 g (3.40 mmol) of potassium carbonate was added to the mixed solution. The mixture was stirred under reflux for 5 hours. After the reaction, the insolubles were filtered off, and the filtrate was concentrated under reduced pressure. The residue was separated by silica gel column chromatography using chloroform alone first, and then a mixture of chloroform and methanol in the volume ratio 30:1 as the eluent. The fractions of the desired compound isolated were concentrated to give 1.55 g (91%) of 2-[2-[4-[(4-chlorophenyl)-2-pyridylmethoxy]-1-piperidyl]ethylthio]-6-methylbenzoxazole as an oil.

Mass analysis value: EI-MS m/e=493(M+), CI-MS m/e=494(M+ +1).

$^1$H-NMR(CDCl$_3$): δ(ppm)=1.74(2H, b), 1.87(2H, b), 2.25(2H, b), 2.42(3H, t), 2.76(2H, t), 2.80(2H, b), 3.42(2H, t), 3.48(1H, m), 5.60(2H, s), 7.04–7.70(10H, m), 8.50(1H, m)

EXAMPLE 9

Using 4-[(4-chlorophenyl)-2-pyridylmethoxy]piperidine and 2-(3-bromopropylthio)benzoxazole, the reaction was carried out as described in Example 1 to obtain 2-[3-[4-[(4-chlorophenyl-2-pyridylmethoxy]-1-piperidyl]propylthio]benzoxazole as an oil.

Mass analysis value: EI-MS M+no peak, CI-MS m/e=494(M+ +1).

$^1$H-NMR(CDCl$_3$): δ(ppm)=1.73(2H, b), 1.88(2H, b), 2.00(2H, m), 2.12(2H, b), 2.47(2H, t), 2.73(2H, b), 3.34(2H, t), 3.47(1H, m), 5.60(1H, s), 7.11–7.70(11H, m), 8.50(1H, m).

EXAMPLE 10

1.00 g (3.30 mmol) of 4-[(4-chlorophenyl)-2-pyridylmethoxy]piperidine and 0.49 g (3.92 mmol) of 2-bromoethanol were dissolved in 10 ml of acetone, and 0.55 g (3.98 mmol) of potassium carbonate was added to the mixed solution. The mixture was stirred at room temperature for 15 hours. After the reaction, the insolubles were filtered off, and the filtrate was concentrated under reduced pressure. The residue was separated by silica gel column chromatography using a mixture of chloroform and methanol in the volume ratio 20:1 as the eluent. The desired fraction was concentrated under reduced pressure to give 0.64 g (56%) of 2-[4-[(4-chlorophenyl)-2-pyridylmethoxy]-1-piperidyl]ethanol as an oil.

Mass analysis value: EI-MS M+no peak, CI-MS m/e=347(M+ +1).

$^1$H-NMR(CDCl$_3$): δ(ppm)=1.73(2H, b), 1.88(2H, b), 2.22(2H, b), 2.50(2H, t), 2.77(2H, b), 2.98(1H, s), 3.49(1H, m), 3.59(2H, t), 5.60(1H, s), 7.12–7.71(7H, m), 8.50(1H, m).

EXAMPLE 11

To a solution of 2.35 g (6.78 mmol) of 2-[4-[(4-chlorophenyl)-2-pyridylmethoxy]-1piperidyl]ethanol obtained in Example 10 dissolved in 20 ml of toluene was added 0.53 g (13.25 mmol) of sodium hydride (60% dispersion in mineral oil), and 1.25 g (8.14 mmol) of 2-chlorobenzoxazole was added to the mixed solution. The mixture stirred under reflux for 7 hours. After the reaction, the insolubles were filtered off, and the filtrate was concentrated under reduced pressure. The residue was separated by silica gel column chromatography using a mixture of chloroform and methanol in the volume ratio of 40:1 as the developing solvent. The desired fractions was concentrated under reduced pressure to give 1.10 g (35%) of 2-[2-[4-[(4-chlorophenyl)-2-pyridylmethoxy]-1-piperidyl]ethoxy]benzoxazole as an oil.

Mass analysis value: EI-MS M+no peak CI-MS m/e=464(M+ +1).

$^1$H-NMR(CDCl$_3$): δ(ppm)=1.70(2H, b), 1.83(2H, b), 2.24(2H, b), 2.68(2H, t), 2.79(2H, b), 3.46(1H, m), 3.91(2H, t), 5.60(1H, s), 6.98–7.71(11H, m), 8.50(1H, m).

EXAMPLE 12

7.50 g (24.77 mmol) of 4-[(4-chlorophenyl)-2-pyridylmethoxy]piperidine and 6.92 g (27.24 mmol) of N-(2-bromoethyl)phthalimide were dissolved in 60 ml of dioxane, and 4.11 g (29.74 mmol) of potassium carbonate was added. The mixture was stirred at an oil bath temperature of 90° to 100° C. for 3 hours. After the reaction, the insolubles were filtered off, and the filtrate was concentrated under reduced pressure. The residue was separated by silica gel column chromatography using a mixture of ethyl acetate and methanol in the volume ratio 25:1 as an eluent. The desired fraction was concentrated under reduced pressure, and 60 ml of ethanol and 1.61 g (32.16 mmol) of hydrazine (hydrate) were added to the residue, and the mixture was stirred under reflux. After 200 ml of 1N aqueous sodium hydroxide was added to the reaction mixture, the mixture was extracted twice with 200 ml of chloroform. The chloroform extract was dried over anhydrous sodium sulfate and concentrated under reduced pressure to give 3.50 g (41%) of 2-[4-[(4-chlorophenyl)-2-pyridylmethoxy]-1-piperidyl]ethylamine as an oily product.

Mass analysis value: EI-MS M+no peak, CI-MS m/e=346(M+ +1).

$^1$H-NMR(CDCl$_3$): δ(ppm)=1.49(2H, s), 1.73(2H, b), 1.88(2H, b), 2.13(2H, b), 2.36(2H, t), 2.73(2H, b), 2.78(2H, t), 3.46(1H, m), 5.60(1H, s), 7.12–7.72(7H, m), 8.50(1H, m).

EXAMPLE 13

To a mixture of 1.12 g (3.24 mmol) of 2-[4-[(4-chlorophenyl)-2-pyridylmethoxy]-1-piperidyl]ethylamine obtained in Example 12 and 0.60 g (3.91 mmol) of 2-chlorobenzoxazole were added 0.57 g (4.12 mmol) of potassium carbonate and 5 ml of dioxane, and the mixture was stirred under heating at an oil-bath temperature of 80° to 85° C. for 3 hours. After the reaction, the insolubles were filtered off, and the filtrate was concentrated under reduced pressure. The residue was separated by silica gel column chromatography using chloroform as an eluent, and the desired fraction was concentrated under reduced pressure to give 0.72 g (48%) of 2-[2-[4-[(4-chlorophenyl)-2-pyridylmethoxy]-1-piperidyl]ethylamino]benzoxazole as an oil.

Mass analysis value: EI-MS M+ no peak, CI-MS m/e=463(M+ +1).

$^1$H-NMR(CDCl$_3$): δ(ppm)=1.74(2H,b), 1.88(2H,b), 2.20(2H,b), 2.60(2H,t), 2.75(2H,b), 3.52(3H,t+m), 5.60(1H,s), 5.86(1H,b), 6.96–7.21(11H,m), 8.51(1H,m).

EXAMPLE 14

From 2-[2-[4-[(4-chlorophenyl)-2-pyridylmethoxy]-1-piperidyl]ethylamino]benzoxazole obtained in Example 13 and fumaric acid, 2-[2-[4-[(4-chlorophenyl)-2-pyridylmethoxy]-1-piperidyl]ethylamino]benzoxazole fumarate was obtained in the same procedure as described in Example 2.

mp 179°–181° C.

Elemental analysis value: Calcd. (for C$_{30}$H$_{31}$ClN$_4$O$_6$): C 62.23 H 5.40 N 9.68, Found: C 62.23 H 5.39 N 9.60.

EXAMPLE 15

To a mixture of 1.60 g (5.28 mmol) of 4-[(4-chlorophenyl)-2-pyridylmethoxy]piperidine and 1.86 g (8.09 mmol) of 2-(2-chloroethylthio)benzoxazole were added 15 ml of dioxane and 1.12 g (8.09 mmol) of potassium carbonate, and the mixture was stirred under heating at an oil bath temperature of 90° to 95° C. for 8 to 10 hours. After the reaction, the insolubles were filtered off, and the filtrate was concentrated under reduced pressure. The residue was separated by silica gel chromatography using a mixture of chloroform and methanol in the volume ratio of 50:1 as an eluent, and the desired fraction was concentrated under reduced pressure to give 0.52 g (20%) of 2-[2-[4-[(4-chlorophenyl)-2-pyridylmethoxy]-1-piperidyl]ethylthio]benzothiazole as an oil.

Mass analysis value: EI-MS M+ no peak, CI-MS m/e=496(M+ +1).

$^1$H-NMR(CDCl$_3$): δ(ppm)=1.76(2H,b), 1.88(2H,b), 2.27(2H,b), 2.78(2H,t), 2.82(2H,b), 3.50(2H,t), 5.60(1H,s), 7.12–7.86(11H,m), 8.50(1H,m).

EXAMPLE 16

To a mixture of 0.76 g (2.51 mmol) of 4-[(4-chlorophenyl)-2-pyridylmethoxy]piperidine and 0.73 g (2.53 mmol) of 2-(3-bromopropylthio)benzothiazole, were added 6 ml of acetone and 0.35 g (2.53 mmol) of potassium carbonate, and the mixture was stirred at room temperature for 15 hours. After the reaction, the insolubles were filtered off, and the filtrate was concentrated under reduced pressure. The residue was separated by silica gel column chromatography using chloroform alone first, and then a mixture of chloroform and methanol in the volume ratio 30:1 as the eluent, and the desired fraction was concentrated to give 0.52 g (41%) of 2-[3-[4-[(4-chlorophenyl)-2-pyridylmethoxy]-1-piperidyl]propylthio]benzothiazole as an oil.

Mass analysis value: EI-MS M+ no peak, CI-MS m/e=510(M+ +1).

$^1$H-NMR(CDCl$_3$): δ(ppm)=1.76(2H,b), 1.90(2H,b), 2.01(2H,m), 2.19(2H,b), 2.76(2H,b), 3.38(2H,t), 3.48(1H,m), 5.60(1H,s), 7.12–7.87(11H,m), 8.50(1H,m).

EXAMPLE 17

To a mixture of 1.02 g (3.37 mmol) of 4-[(4-chlorophenyl)-2-pyridylmethoxy]piperidine and 0.53 g (3.38 mmol) of 1-bromo-3-chloropropane, were added 7 ml of acetone and 0.47 g (3.40 mmol) of potassium carbonate, and the mixture was stirred at room temperature for 14 hours, and then 0.85 g (4.00 mmol) of 6-ethoxy-2-mercaptobenzothiazole, 0.47 g (3.40 mmol) of potassium carbonate and 0.20 g (1.20 mmol) of potassium iodide were added, and the mixture was again stirred under reflux for 15 hours. After the reaction, the insolubles were filtered off, and the filtrate was concentrated under reduced pressure. The residue was separated by silica gel column chromatography using chloroform first, and then a mixture of chloroform and methanol in the volume ratio of 30:1 as the eluent, and the desired fraction was concentrated under reduced pressure to give 1.00 g (53%) of 2-[3-[4-[(4-chlorophenyl)-2-pyridylmethoxy]-1-1-piperadyl]propylthio]-6-ethoxybenzothiazole as an oil.

Mass analysis value: EI-MS m/e=553(M+), CI-MS m/e=554(M+ +1).

$^1$H-NMR(CDCl$_3$): δ(ppm)=1.43(3H,t), 1.73(2H,b), 1.88(2H,b), 1.97(2H,m), 2.12(2H,b), 2.46(2H,t), 2.72(2H,b), 3.33(2H,t), 3.46(1H,m), 4.06(2H,q), 5.60(1H,s), 6.97–7.74(10H,m), 8.50(1H,m).

EXAMPLE 18

From 2-[3-[4-[(4-chlorophenyl)-2-pyridylmethoxy]-1-piperidyl]propylthio]-6-ethoxybenzothiazole obtained in Example 17 and fumaric acid, 2-[3-[4-[(4-chlorophenyl)-2-pyridylmethoxy]-1-piperidyl]propylthio]-6-ethoxybenzothiazole fumarate was obtained in the same procedure as described in Example 2.

mp 144°–147° C.

Elemental analysis value: Calcd. (for $C_{33}H_{36}ClN_3O_6S_2$ $H_2O$): C 57.59 H 5.57 N 6.10, Found: C 57.76 H 5.26 N 5.74.

EXAMPLE 19

From 2-[4-[(4-chlorophenyl)-2-pyridylmethoxy]-1-piperidyl]ethylamine and 2-chlorobenzothiazole, 2-[2-[4-[(4-chlorophenyl)-2-pyridylmethoxy]-1-piperidyl]ethylamino]benzothiazole was obtained as an oil in the same procedure as described in Example 13.

Mass analysis value: EI-MS M+ no peak, CI-MS m/e=479(M++1).

$^1$H-NMR(CDCl$_3$): δ(ppm)=1.75(2H,b), 1.90(2H,b), 2.22(2H,b), 2.61(2H,t), 2.75(2H,b), 3.47(3H,t+m), 5.60(1H,s), 5.95(1H,b), 7.03–7.72(11H,m), 8.50(1H,m).

EXAMPLE 20

To a mixture of 1.00 g (3.96 mmol) of 4-(diphenylmethyl)-piperazine and 1.28 g (5.57 mmol) of 2-(2-chloroethylthio)benzothiazole, were added 10 ml of dioxane, 2 ml of dimethylformamide and 0.85 g (6.15 mmol) of potassium carbonate, and the mixture was stirred under reflux for 3 hours. After the reaction, the insolubles were filtered off, and the filtrate was concentrated. The residue was separated by silica gel column chromatography using a mixture of chloroform and methanol in the volume ratio 30:1 as the developing solvent, and the desired fraction was concentrated under reduced pressure to give 0.61 g (35%) of 2-[2-[4-(diphenylmethyl)-1-piperadinyl]-ethylthio]benzothiazole as an oil.

Mass analysis value: EI-MS M+ no peak, CI-MS m/e=446(M++1).

$^1$H-NMR(CDCl$_3$): δ(ppm)=2.44(4H,b), 2.57(4H,b), 2.78(2H,t), 3.50(2H,t), 4.22(1H,s), 7.13–7.42(12H,m), 7.70(1H,dd), 7.83(1H,dd).

EXAMPLE 21

Using 4-(diphenylmethyl)piperazine, 1-bromo-3-chloropropane and 2-mercaptobenzimidazole, the reaction was carried out in the same procedure as described in Example 17, and the obtained crystals were recrystallized from hexane to give 2-[3-[4-(diphenylmethyl)-1-piperadinyl]propylthio]benzothiazole. mp 104°–105° C.

Mass analysis value: EI-MS m/e=459(M+), CI-MS m/e=460(M++1).

$^1$H-NMR(CDCl$_3$): δ(ppm)=2.00(2H,m), 2.46(10H,b+t), 3.37(2H,t), 4.22(1H,s), 7.13–7.43(12H,m), 7.73(1H,dd), 7.83(1H,dd).

EXAMPLE 22

0.70 g (1.52 mmol) of 2-[3-[4-(diphenylmethyl)-1-piperadinyl]propylthio]benzothiazole obtained in Example 21 was dissolved in 15 ml of ethanol, and 0.40 g (3.45 mmol) of maleic acid was added to the solution, and then the mixture was stirred at room temperature for about 2 hours. The precipitated crystals were collected, and recrystallized from ethanol to give 2-[3-[4-(diphenylmethyl)-1-piperadinyl]propylthio]benzothiazole dimaleate.

mp 165°–166° C.

Elemental analysis value: Calcd. (for $C_{35}H_{37}N_3O_8S_2$ $\frac{1}{4}H_2O$): C 60.37 H 5.42 N 6.03, Found: C 60.62 H 5.39 N 5.59.

EXAMPLE 23

Using 4-(diphenylmethyl)piperazine, 1-bromo-3-chloropropane and 2-mercaptobenzimidazole, the reaction was carried out in the same procedure as described in Example 18 to give 2-[3-[4-(diphenylmethyl)-1-piperadinyl]-propylthio]benzimidazole as a foam.

Mass analysis value: EI-MS M+ no peak, CI-MS m/e=443(M++1).

$^1$H-NMR(CDCl$_3$): δ(ppm)=2.01(2H,m), 2.44(1H,b), 2.66(8H,b), 2.73(2H,t), 3.23(2H,t), 4.47(1H,s), 7.14–7.48(14H,m).

EXAMPLE 24

2.00 g (6.61 mmol) of 4-[(4-chlorophenyl)-2-pyridylmethoxy]piperidine and 1.43 g (7.90 mmol) of ethyl 3-bromopropionate were dissolved in 10 ml of dioxane, and 1.09 g (7.89 mmol) of potassium carbonate was added to the mixed solution, and then the mixture was stirred under heating at an oil bath temperature of around 80° C. for 8 hours. After the reaction, the insolubles were filtered off, and the filtrate was concentrated under reduced pressure. The residue was separated by silica gel column chromatography using a solvent mixture of chloroform and methanol in the volume ratio 19:1 as are eluent. The desired fraction was concentrated under reduced pressure to give 1.78 g (67%) of ethyl 3-[4-[(4-chlorophenyl)-2-pyridylmethoxy]-1-piperidyl]-propionate.

mp 155°–156° C.

Mass analysis value: EI-MS M+ no peak, CI-MS m/e=403(M++1).

$^1$H-NMR(CDCl$_3$): δ(ppm)=1.25(3H,t), 2.02(2H,b), 2.28(2H,b), 2.85–3.17(8H,m), 3.74(1H,m), 4.16(2H,q), 5.56(1H,s), 7.17–7.73(7H,m), 8.52(1H,m).

EXAMPLE 25

1.00 g (2.48 mmol) of ethyl 3-[4-[(4-chlorophenyl)-2-pyridylmethoxy]-1-piperidyl]propionate obtained in Example 24 was dissolved in a mixed solution of 1 ml of 50 wt % of aqueous sodium hydroxide and 8 ml of ethanol, and the solution was stirred at room temperature for 2 hours. The reaction mixture was concentrated under reduced pressure, neutralized with dil. hydrochloric acid and then extracted with chloroform. The chloroform extract was dried over anhydrous sodium sulfate and then concentrated to give 0.86 g (92%) of 3-[4-[(4-chlorophenyl)-2-pyridylmethoxy]-1-piperidyl]-propionic acid.

Mass analysis value: EI-MS M+ no peak, CI-MS m/e=375(M++1).

$^1$H-NMR(CDCl$_3$): δ(ppm)=1.92(4H,b), 2.51(2H,t), 2.58(2H,b), 2.27(2H,t), 2.90(2H,b), 3.65(1H,m), 5.58(1H,s), 7.15–7.74(7H,m), 8.52(1H,m).

EXAMPLE 26

After 4.98 g (16.45 mmol) of 4-[(4-chlorophenyl)-2-pyridylmethoxy]piperidine and 3.85 g (19.74 mmol) of ethyl 4-bromobutanoate were dissolved in 35 ml of acetone, 2.73 g (19.75 mmol) of potassium carbonate was added to the mixed solution, and the mixture was stirred under reflux by heating for 4 hours. The insolubles were filtered off, and the filtrate was concentrated under reduced pressure. The residue was separated by silica gel column chromatography using a solvent mixture of chloroform and methanol in the volume ratio of 30:1 as an eluent. The desired fraction was concentrated under reduced pressure to give 6.26 g (91%) of ethyl 4-[4-[(4-chlorophenyl)-2-pyridylmethoxy]-1-piperidyl]-butanoate as an oil.

Mass analysis value: EI-MS M+ no peak, CI-MS m/e=417(M++1).

$^1$H-NMR(CDCl$_3$): δ(ppm)=1.13(3H,t), 1.10–1.98(6H,b,m), 2.12(2H,b), 2.33(4H,t), 2.70(2H,b), 3.45(1H,m), 4.11(2H,q), 5.59(1H,s), 7.12–7.72(7H,m), 8.50(1H,m).

EXAMPLE 27

5.33 g (12.78 mmol) of the ethyl ester obtained in Example 26 and 2.43 g (12.78 mmol) of p-toluenesulfonic acid were treated in the same procedure as described in Example 2 to give 6.88 g (91%) of ethyl 4-[4-[(4-chlorophenyl)-2-pyridylmethoxy]-1-piperidyl]-butanoate p-toluenesulfonate.

mp 130°–132° C.

Elemental analysis value: Calcd. (for C$_{23}$H$_{29}$ClN$_2$O$_3$ C$_7$H$_8$O$_3$S): C 61.16 H 6.33 N 4.76, Found: C 61.14 H 6.25 N 4.75.

EXAMPLE 28

From ethyl 4-[4-[(4-chlorophenyl)-2-pyridylmethoxy]-1-piperidyl]butanoate obtained in Example 26, 4-[4-[(4-chlorophenyl)-2-pyridylmethoxy]-1-piperidyl]-butanoic acid was obtained in the same procedure as described in Example 25.

Mass analysis value: EI-MS M+ no peak, CI-MS m/e=389(M++1).

$^1$H-NMR(CDCl$_3$): δ(ppm)=1.84–1.98(6H,b,m), 2.58(2H,t), 2.73(4H,b,m), 2.92(2H,b), 3.68(1H,m), 7.17–7.22(7H,m), 8.51(1H,m), 11.31(1H,b).

EXAMPLE 29

0.50 g (1.29 mmol) of 4-[4-[(4-chlorophenyl)-2-pyridylmethoxy]-1-piperidyl]butanoic acid obtained in Example 28 was dissolved in 5 ml of dichloromethane, and 0.32 g (1.55 mmol) of dicyclohexylcarbodiimide was added to the reaction mixture on an ice bath. Then, 10 ml of ammonia gas dissolved dichloromethane solution was added, and the mixture was stirred at room temperature for 10 hours. After the reaction, the insolubles were filtered off, and the filtrate was concentrated under reduced pressure. The residue was separated by silica gel column chromatography using a mixture of chloroform, methanol and conc. ammonia water (conc. 25% by weight) in the volume ratio 90:9:1 as the eluent. The desired fraction was concentrated under reduced pressure to give 0.38 g (76%) of 4-[4-[(4-chlorophenyl)-2-pyridylmethoxy]-1-piperidyl]butanamide as an oil.

Mass analysis value: EI-MS M+ no peak, CI-MS m/e=388(M++1).

$^1$H-NMR(CDCl$_3$): δ(ppm)=1.58–1.97(6H,b,m), 2.10(2H,b), 2.23(2H,t), 2.31(2H,t), 2.72(2H,b), 3.45(1H,m), 5.61(1H,s), 6.30(1H,b,s), 6.82(1H,b,s), 7.11–7.70(7H,m), 8.51(1H,m).

EXAMPLE 30

0.38 g (0.98 mmol) of the amide obtained in Example 29 was dissolved in 3 ml of ethanol, and 0.11 g (0.98 mmol) of maleic acid was added. The precipitated white crystals were recrystallized from ethyl acetate to give 0.35 g (71%) of 4-[4-[(4-chlorophenyl)-2-pyridylmethoxy]-1-piperidyl]butanamide maleate.

mp 123.5°–124.5° C.

Elemental analysis value: Calcd. (for C$_{21}$H$_{26}$N$_3$O$_2$Cl C$_4$H$_4$O$_4$): C 59.58 H 6.00 N 8.34, Found: C 59.68 H 5.85 N 8.36.

EXAMPLE 31

From 4-[(4-chlorophenyl)-2-pyridylmethoxy]piperidine and N,N-dimethyl-4-chlorobutaneamide, N,N-dimethyl-4-[4-[(4-chlorophenyl)-2-pyridylmethoxy]-1-piperidyl]butanamide was obtained in the same procedure as in Example 24.

Mass analysis value: EI-MS M+ no peak, CI-MS m/e=416(M++1).

$^1$H-NMR(CDCl$_3$): δ(ppm)=1.62–2.00(6H,b,m), 2.16(2H,b), 2.33(2H,t), 2.38(2H,t), 2.75(2H,b), 2.92(3H,s), 3.00(3H,s), 3.46(1H,m), 5.60(1H,s), 7.12–7.71(7H,m), 8.50(1H,m).

EXAMPLE 32

From 4-[(4-chlorophenyl)-2-pyridylmethoxy]-piperidine and propyl 4-chlorobutanoate, propyl 4-[4-[(4-chlorophenyl)-2-pyridylmethoxy]-1-piperidyl]-butanoate was obtained in the same procedure as described in Example 26.

Mass analysis value: EI-MS M+ no peak, CI-MS m/e=431(M++1).

$^1$H-NMR(CDCl$_3$): δ(ppm)=0.92(3H,t), 1.55–1.96(8H,m), 2.10(2H,b), 2.32(4H,t), 2.71(2H,b), 3.45(1H,m), 4.01(2H,t), 5.60(1H,s), 7.12–7.71(7H,m), 8.50(1H,m).

EXAMPLE 33

From the propyl ester obtained in Example 32 and p-toluenesulfonic acid, propyl 4-[4-[(4-chlorophenyl)-2-pyridylmethoxy]-1-piperidyl]butanoate p-toluenesulfonate was obtained in the same procedure as described in Example 2.

mp 122°–123° C.

Elemental analysis value: Calcd. (for C$_{24}$H$_{31}$ClN$_2$O$_3$ C$_7$H$_8$O$_3$S): C 61.73 H 6.52 N 4.64, Found: C 61.61 H 6.57 N 4.64.

EXAMPLE 34

From 4-diphenylmethoxypiperidine and ethyl 4-bromobutanoate, ethyl 4-(4-diphenylmethoxy-1-piperidyl)-butanoate was obtained in the same procedure as in Example 26.

Mass analysis value: EI-MS M+ no peak, CI-MS m/e=382(M++1).

$^1$H-NMR(CDCl$_3$): δ(ppm)=1.24(3H,t), 1.17–1.98(6H,b,m), 2.15(2H,b), 2.31(2H,t), 2.36(2H,t), 2.75(2H,b), 3.44(1H,m), 4.12(2H,q), 5.51(1H,s), 7.20–7.40(10H,m).

EXAMPLE 35

From the ethyl ester obtained in Example 34 and fumaric acid, ethyl 4-(4-diphenylmethoxy-1-piperidyl)-butanoate fumarate, was obtained in the same procedure as described in Example 2.

mp 106°–107° C.

Elemental analysis value: Calcd. (for C$_{24}$H$_{31}$O$_3$N C$_4$H$_4$O$_4$ ½H$_2$O): C 66.39 H 7.16 N 2.76, Found: C 66.44 H 7.01 N 2.71.

EXAMPLE 36

From 4-(phenyl-2-pyridylmethoxy)piperidine and ethyl 4-bromobutanoate, ethyl 4-[4-(phenyl-2-pyridylmethoxy)-1-piperidyl]butanoate was obtained in the same procedure as described in Example 26.

Mass analysis value: EI-MS M+ no peak, CI-MS m/e=383(M+ +1).

$^1$H-NMR(CDCl$_3$): δ(ppm)=1.24(3H,t), 1.65–2.00(6H,b,m), 2.11(2H,b), 2.31(4H,m), 2.72(2H,b), 3.47(1H,m), 4.11(2H,q), 5.64(1H,s), 7.10–7.70(8H,m), 8.50(1H,m).

EXAMPLE 37

From the ethyl ester obtained in Example 36 and p-toluenesulfonic acid, ethyl 4-[4-(phenyl-2-pyridylmethoxy)-1-piperidyl]butanoic acid p-toluenesulfonate, was obtained in the same procedure as in Example 2.

mp 84°–85° C.

Elemental analysis value: Calcd. (for C$_{23}$H$_{30}$N$_2$O$_3$ C$_7$H$_8$O$_3$S ½H$_2$O): C 63.92 H 6.97 N 4.97, Found: C 63.79 H 6.83 N 4.97.

EXAMPLE 38

From 4-[(4-chlorophenyl)phenylmethoxy)piperidine and ethyl 4-bromobutanoate, ethyl 4-[4-[(4-chlorophenyl)-phenylmethoxy]-1-piperidyl]butanoate was obtained in the same procedure as described in Example 26.

Mass analysis value: EI-MS M+ no peak, CI-MS m/e=416(M+ +1).

$^1$H-NMR(CDCl$_3$): δ(ppm)=1.24(3H,t), 1.63–1.93(6H,b,m), 2.10(2H,b), 2.32(4H,t), 2.70(2H,b), 3.40(1H,m), 4.11(2H,q), 5.47(1H,s), 7.28(9H,m).

EXAMPLE 39

From the ethyl ester obtained in Example 38 and p-toluenesulfonic acid, ethyl 4-[4-[(4-chlorophenyl)-phenylmethoxy]-1-piperidyl]butanoate p-toluenesulfonate, was obtained in the same procedure as described in Example 3-b.

mp 92°–94° C.

Elemental analysis value: Calcd. (for C$_{24}$H$_{30}$ClNO$_3$ C$_7$H$_8$O$_3$S ¼H$_2$O): C 62.82 H 6.55 N 2.36, Found: C 62.85 H 6.53 N 2.33.

EXAMPLE 40

From 4-(phenyl-3-pyridylmethoxy)piperidine and ethyl 4-bromobutanoate, ethyl 4-[4-phenyl-3-pyridylmethoxy]-1-piperidyl]butanoate was obtained in the same procedure as described in Example 26.

Mass analysis value: EI-MS M+ no peak, CI-MS m/e=383(M+ +1).

$^1$H-NMR(CDCl$_3$): δ(ppm)=1.24(3H,t), 1.62–1.96(6H,b,m), 2.12(2H,b), 2.32(4H,m), 2.72(2H,b), 3.44(1H,m), 4.12(2H,q), 5.53(1H,s), 7.20–7.36(6H,m), 7.63(1H,m), 8.49(1H,m), 8.60(1H,d).

EXAMPLE 41

From the ethyl ester obtained in Example 40 and p-toluenesulfonic acid, ethyl 4-[4-(phenyl-3-pyridylmethoxy]-1-piperidyl]butanoate p-toluenesulfonate, was obtained in the same procedure as described in Example 2.

mp 101.5°–103° C.

Elemental analysis value: Calcd. (for C$_{23}$H$_{30}$N$_2$O$_3$ C$_7$H$_8$O$_3$S ¼H$_2$O): C 64.44 H 6.94 N 5.01, Found: C 64.29 H 6.94 N 4.83.

EXAMPLE 42

From 4-[bis(4-methoxyphenyl)methoxy]piperidine and ethyl 4-bromobutanoate, ethyl 4-[4-[bis(4-methoxyphenyl)-methoxy]-1-piperidyl]butanoate was obtained in the same procedure as described in Example 26.

Mass analysis value: EI-MS M+ no peak, CI-MS m/e=442(M+ +1).

$^1$H-NMR(CDCl$_3$): δ(ppm)=1.23(3H,t), 1.62–1.93(6H,b,m), 2.09(2H,b), 2.30(4H,m), 2.72(2H,b), 3.39(1H,m), 3.76(6H,s), 4.11(2H,q), 5.43(1H,m), 6.83(4H,m), 7.22(4H,m).

EXAMPLE 43

From the ethyl ester obtained in Example 42 and p-toluenesulfonic acid, ethyl 4-[4-[bis(4-methoxyphenyl)-methoxy]-1-piperidyl]butanoate p-toluenesulfonate was obtained in the same procedure as described in Example 2.

mp 93°–95.5° C.

Elemental analysis value: Calcd. (for C$_{26}$H$_{35}$O$_5$N C$_7$H$_8$O$_3$S): C 64.58 H 7.06 N 2.28, Found: C 64.37 H 7.31 N 2.64.

EXAMPLE 44

From 4-[bis(4-fluorophenyl)methoxy]piperidine and ethyl 4-bromobutanoate, ethyl 4-[4-[bis(4-fluorophenyl)-methoxy]-1-piperidyl]butanoate was obtained in the same procedure as described in Example 26.

Mass analysis value: EI-MS M+ no peak, CI-MS m/e=418(M+ +1).

$^1$H-NMR(CDCl$_3$): δ(ppm)=1.24(3H,t), 1.63–1.92(6H,b,m), 2.13(2H,b), 2.33(4H,m), 2.74(2H,b), 3.38(1H,m), 4.12(2H,q), 5.46(1H,s), 7.00(4H,m), 7.28(4H,m).

EXAMPLE 45

From the ethyl ester obtained in Example 44 and p-toluenesulfonic acid, ethyl 4-[4-[bis(4-fluorophenyl)-methoxy]-1-piperidyl]butanoate p-toluenesulfonate, melting at 122° to 123° C. was obtained in the same procedure as described in Example 2.

Elemental analysis value: Calcd. (for C$_{24}$H$_{29}$F$_2$NO$_3$ C$_7$H$_8$O$_3$S ½H$_2$O): C 62.19 H 6.40 N 2.34, Found: C 62.29 H 6.49 N 2.37.

EXAMPLE 46

From 4-[(4-chlorophenyl)-2-pyridylmethoxy]piperidine and ethyl 4-bromo-2-butenoate, ethyl 4-[4-[(4-chlorophenyl)-2-pyridylmethoxy]-1-piperidyl]-2-butenoate was obtained in the same procedure as described in Example 26.

Mass analysis value: EI-MS M+ no peak, CI-MS m/e=415(M+ +1).

$^1$H-NMR(CDCl$_3$): δ(ppm)=1.27(2H,t), 1.78(2H,b), 1.90(2H,b), 2.24(2H,b), 2.75(2H,b), 3.13(2H,dd), 3.49(1H,m), 4.18(2H,q), 5.59(1H,s), 5.96(1H,m), 6.93(1H,dt), 7.13–7.72(7H,m), 8.50(1H,m).

EXAMPLE 47

From 4-[(4-chlorophenyl)-2-pyridylmethoxy]piperidine and 5-chloro-2-pentanone, 5-[4-[(4-chlorophenyl)-2-pyridylmethoxy]-1-piperidyl]-2-pentanone was obtained in the same procedure as described in Example 26.

Mass analysis value: EI-MS M+ no peak, CI-MS m/e=387(M+ +1).

$^1$H-NMR(CDCl$_3$): δ(ppm)=1.60–1.95(6H,b,m), 2.08(2H,b), 2.14(3H,s), 2.27(2H,t), 2.43(2H,t), 2.70(2H,b), 3.44(1H,m), 5.59(1H,s), 7.11–7.71(7H,m), 8.50(1H,m).

EXAMPLE 48

From the ketone obtained in Example 47 and fumaric acid, 5-[4-[(4-chlorophenyl)-2-pyridylmethoxy]-1-piperidyl]-2-pentanonefumarate was obtained in the same procedure as described in Example 2.

mp 113°–114.5° C.

Elemental analysis value: Calcd. (for C$_{22}$H$_{27}$ClN$_2$O$_2$ C$_4$H$_4$O$_4$ ¼H$_2$O): C 61.53 H 6.25 N 5.52, Found: C 61.50 H 6.15 N 5.37.

EXAMPLE 49

From 4-[(4-chlorophenyl)-2-pyridylmethoxy]piperidine and 3-chloro-1-benzoylpropane, 4-[(4-chlorophenyl)-2-pyridylmethoxy]-1-(3-benzoylpropyl)piperidine was obtained in the same procedure as described in Example 26.

Mass analysis value: EI-MS M$^+$ no peak, CI-MS m/e=449(M$^+$+1).

$^1$H-NMR(CDCl$_3$): δ(ppm)=1.88(2H,b), 2.11(4H,b,m), 2.67(4H,b), 2.94(2H,b), 3.10(2H,t), 3.63(1H,m), 5.57(1H,s), 7.14–7.72(10H,m), 7.96(2H,m), 8.51(1H,m).

EXAMPLE 50

From 4-[(4-chlorophenyl)-2-pyridylmethoxy]piperidine and 3-chloro-1-(4-tert-butylbenzoyl)propane, 4-[(4-chlorophenyl)-2-pyridylmethoxy]-1-[3-(4-tert-butylbenzoyl)propyl]piperidine was obtained in the same procedure as described in Example 24.

Mass analysis value: EI-MS M$^+$ no peak, CI-MS m/e=505(M$^+$+1).

$^1$H-NMR(CDCl$_3$): δ(ppm)=1.33(9H,s), 1.68(2H,b), 1.90(4H,b,m), 2.14(2H,b), 2.39(2H,t), 2.73(2H,b), 2.97(2H,t), 3.45(1H,m), 5.59(1H,s), 7.12–7.71(9H,m), 7.90(2H,m), 8.50(1H,m).

As described above, the novel compounds from the present invention provide pharmaceutical compositions with pharmacological or pharmaceutical activities, particularly antihistaminic activity or antiallergic activity, and give the great industrial importance.

We claim:

1. A compound represented by Formula (I):

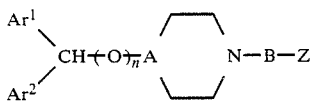

wherein Ar$^1$ and Ar$^2$ each independently represent a group selected from the group consisting of a phenyl group; phenyl groups having a halogen atom, a nitro group, a lower alkoxy group, a lower alkyl group or a lower alkyl group substituted with halogen atoms; and a pyridyl group; n is an integer of 0 or 1; A is a group selected from the group consisting of >N— and >CH—, with the proviso that when A is >N—, n is 0, and when A is >CH—, n is 1; B represents an alkylene group or an alkenylene which may be a straight chain having 2 to 6 carbon atoms or a branched chain having at least 2 carbon atoms in the main chain; Z is represented by Formula (II):

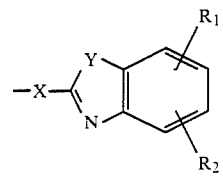

(wherein X and Y each independently represent a group selected from the group consisting of >NH, —O— and —S—, R$_1$ and R$_2$ each independently represent a group selected from the group consisting of a hydrogen atom, halogen atoms, a lower alkyl group and a lower alkoxy group) or a group of Formula (II'):

(wherein Z' represents a group selected from the group consisting of a lower alkyl group, hydroxyl group, a lower alkoxy group, a phenoxy group, an amino group, a lower alkylamino group, an anilino group, a phenyl group and phenyl groups substituted with a lower alkyl group, with the proviso that when Z' is a phenyl group or a phenyl group substituted with a lower alkyl group, at least either one of said Ar$^1$ and Ar$^2$ is a pyridyl group, and, when Z is represented by Formula (II'), A is >CH and n is 1), or its pharmaceutically acceptable acid adduct.

2. The compound according to claim 1, wherein at least one of Ar$^1$ and Ar$^2$ is a pyridyl group.

3. The compound according to claim 1, wherein at least one of Ar$^1$ and Ar$^2$ is a phenyl group having a halogen atom.

4. The compound according to claim 1, wherein B is at least one selected from the group consisting of a staright alkylene group and a straight alkenylene group having 2 to 5 carbon atoms.

5. The compound according to claim 1, wherein Z represents the group of Formula (II).

6. The compound according to claim 5, wherein one of R$_1$ and R$_2$ represents a hydrogen atom and another one of R$_1$ and R$_2$ represents one selected from the group consisting of hydrogen atom, chlorine atom, a methyl group and an ethoxy group; X is —S—; and Y is —O— or —S—.

7. The compound according to claim 6, wherein one of Ar$^1$ and Ar$^2$ is a pyridyl group and another one is a phenyl group having halogen atom.

8. The compound according to claim 7, wherein one of Ar$^1$ and Ar$^2$ is a 4-chlorophenyl group and another one is a 2-pyridyl group.

9. The compound according to claim 1, wherein Z represents the group of Formula (II').

10. The compound according to claim 9, wherein Z' is at least one selected from the group consisting of a lower alkoxy group and a hydroxy group.

11. The compound according to claim 9, wherein one of Ar$^1$ and Ar$^2$ is a pyridyl group and another one is a phenyl group having halogen atom.

12. The compound according to claim 11, wherein one of Ar$^1$ and Ar$^2$ is a 4-chlorophenyl group and another one is a 2-pyridyl group.

13. The compound according to claim 12, wherein A is >CH—; n is 1; B is propylene group, and Z' is an ethoxy group.

14. The compound according to claim 13, wherein the compound is the p-toluenesulfonic acid adduct.

15. An antihistaminic and antiallergic pharmaceutical composition which comprises the compound or its pharmaceutically acceptable acid adduct as described in claim 1 as an active component.

16. The compound of claim 1 which is 2-[2-[4-[(4-Chlorophenyl)-2-pyridylmethoxy]-1-piperidyl]-ethylthio]benzoxazole.

17. The compound of claim 1 which is 5-Chloro-2-[2-[4-[(4-chlorophenyl)-2-pyridylmethoxy]-1-piperidyl]ethylthio]benzoxazole.

18. The compound of claim 1 which is 5-Chloro-2-[2-[4-(diphenylmethoxy)-1-piperidyl]ethylthio]benzoxazole.

19. The compound of claim 1 which is 2-[2-[4-[(4-Chlorophenyl)-2-pyridylmethoxy]-1-piperidyl]-ethylthiobenzoxazole fumarate.

20. The compound of claim 1 which is 2-[3-[4-[(4-Chlorophenyl)-2-pyridylmethoxy]-1-piperidyl]-propylthio]benzoxazole.

21. The compound of claim 1 which is 2-[2-[4-[(4-Chlorophenyl)-2-pyridylmethoxy]-1-piperidyl]-ethylthio]-6-methylbenzoxazole.

22. The compound of claim 1 which is 2-[2-[4-[(4-Chlorophenyl)-2-pyridylmethoxy]-1-piperidyl]-ethyloxy]benzoxazole.

23. The compound of claim 1 which is 2-[2-[4-[(4-Chlorophenyl)-2-pyridylmethoxy]-1-piperidyl]-ethylamino]benzoxazole.

24. The compound of claim 1 which is 2-[2-[4-[(4-Chlorophenyl)-2-pyridylmethoxy]-1-piperidyl]-ethylamino]benzoxazole fumarate.

25. The compound of claim 1 which is 2-[2-[4-[(4-Chlorophenyl)-2-pyridylmethoxy]-1-piperidyl]-ethylthio]benzothiazole.

26. The compound of claim 1 which is 2-[3-[4-[(4-Chlorophenyl)-2-pyridylmethoxy]-1-piperidyl]-propylthio]benzothiazole.

27. The compound of claim 1 which is 2-[3-[4-[(4-Chlorophenyl)-2-pyridylmethoxy]-1-piperidyl]-propylthio]-6-ethoxybenzothiazole.

28. The compound of claim 1 which is 2-[2-[4-[(4-Chlorophenyl)-2-pyridylmethoxy]-1-piperidyl]-ethylamino]benzothiazole.

29. The compound of claim 1 which is 2-[2-[4-(Diphenylmethyl)-1-piperadinyl]ethylthio]benzothiazole.

30. The compound of claim 1 which is 2-[3-[4-(Diphenylmethyl)-1-piperadinyl]propylthio]benzothiazole.

31. The compound of claim 1 which is 2-[3-[4-(Diphenylmethyl)-1-piperadinyl]propylthio]benzothiazole dimaleate.

32. The compound of claim 1 which is 2-[3-[4-(Diphenylmethyl)-1-piperadinyl]propylthio]benzimidazole.

33. The compound of claim 1 which is 3-[4-[(4-Chlorophenyl)-2-pyridylmethoxy]-1-piperidyl]-propionic acid.

34. The compound of claim 1 which is Ethyl 3-[4-[(4-chlorophenyl)-2-pyridylmethoxy]-1-piperidyl]propionate.

35. The compound of claim 1 which is 4-[4-[(4-Chlorophenyl)-2-pyridylmethoxy]-1-piperidyl]-butanoic acid.

36. The compound of claim 1 which is Ethyl 4-[4-[(4-chlorophenyl)-2-pyridylmethoxy]-1-piperidyl]butanoate or its p-toluenesulfonic acid adduct.

37. The compound of claim 1 which is 4-[4-[(4-Chlorophenyl)-2-pyridylmethoxy]-1-piperidyl]-butaneamide or its maleic acid adduct.

38. The compound of claim 1 which is Ethyl 4-(4-diphenylmethoxy-1-piperidyl)butanoate or its fumaric acid adduct.

39. The compound of claim 1 which is Ethyl 4-[4-(phenyl-2-pyridylmethoxy)-1-piperidyl]butanoate or its p-toluenesulfonate.

40. The compound of claim 1 which is Ethyl 4-[4-(phenyl-3-pyridylmethoxy)-1-piperidyl]butanoate or its p-toluenesulfonate.

41. The compound of claim 1 which is Ethyl 4-[4-[(4-chlorophenyl)-phenylmethoxy]-1-piperidyl]butanoate or its p-toluenesulfonate.

42. The compound of claim 1 which is Ethyl 4-[4-(4,4'-dimethoxyphenylmethoxy)-1-piperidyl]-butanoate or its p-toluenesulfonate.

43. The compound of claim 1 which is Ethyl 4-[4-(4,4'-difluorophenylmethoxy)-1-piperidyl]-butanoate or its p-toluenesulfonate.

44. The compound of claim 1 which is Ethyl 4-[4-[(4-methylphenyl)-phenylmethoxy]-1-piperidyl]-butanoate.

45. The compound of claim 1 which is Propyl 4-[4-[(4-chlorophenyl)-2-pyridylmethoxy]-1-piperidyl]-butanoate or its p-toluenesulfonate.

46. The compound of claim 1 which is Ethyl 4-[4-[(4-chlorophenyl)-2-pyridylmethoxy]-1-piperidyl]-2-butenoate.

47. The compound of claim 1 which is 5-[4-[(4-Chlorophenyl)-2-pyridylmethoxy]-1-piperidyl]-2-pentanone or its fumarate.

48. The compound of claim 1 which is 4-[(4-Chlorophenyl)-2-pyridylmethoxy]-1-(3-benzoylpropyl)piperidine.

49. The compound of claim 1 which is 4-[(4-Chlorophenyl)-2-pyridylmethoxy]-1-[3-(4-tert-butylbenzoyl)propyl]piperidine.

* * * * *